United States Patent [19]

Krauss

[11] Patent Number: 4,835,393
[45] Date of Patent: May 30, 1989

[54] METHOD AND APPARATUS FOR DETERMINING CONCENTRATION

[75] Inventor: Lutz Krauss, Sindelfingen, Fed. Rep. of Germany

[73] Assignee: Deutsche Forschungs- und Versuchsanstalt fur Luft- und Raumfahrt e.V., Bonn, Fed. Rep. of Germany

[21] Appl. No.: 57,945

Related U.S. Application Data

[63] Continuation at PCT PE86/00173 filed Apr. 23, 1986, published as WO87/02772

[22] Filed: Jun. 4, 1987

[30] Foreign Application Priority Data

Oct. 22, 1985 [DE] Fed. Rep. of Germany ....... 3537482

[51] Int. Cl.$^4$ .......................... G01J 1/42; G01N 21/00
[52] U.S. Cl. ..................................... 250/373; 356/437; 356/438
[58] Field of Search ................ 250/373, 372; 356/432, 356/433, 434, 436, 437, 438, 439

[56] References Cited

U.S. PATENT DOCUMENTS 4,536,090  8/1985  Schmidt et al. ................ 250/373 X

FOREIGN PATENT DOCUMENTS 2246365  9/1972  Fed. Rep. of Germany.
2343097  8/1973  Fed. Rep. of Germany.
2910673  3/1974  Fed. Rep. of Germany.
2546565  10/1975  Fed. Rep. of Germany.
3334264  9/1983  Fed. Rep. of Germany.

OTHER PUBLICATIONS

Analytical Chemistry, "Generation of Formaldehyde in Test Atmospheres with Low Concentrations of Hydrogen and Carbon Monoxide", 1983, pp. 1440–1442.
Technisches Messen, Band 50, No. 11, Nov. 1983, pp. 417–422.

Primary Examiner—Eugene R. LaRoche
Assistant Examiner—David Mis
Attorney, Agent, or Firm—Wolf, Greenfield & Sacks

[57] ABSTRACT

To improve the accuracy and reduce the sensitivity of interference absorptions in a method for determining the concentration of formaldehyde in a medium by an absorption measurement in the range of at least one characteristic absorption band of the formaldehyde and, in the appropriate instance, subtraction of an interference absorption which is determined by at least one absorption measurement in a wavelength range outside of the characteristic absorption band of the formaldehyde, it is proposed that a discharge be maintained at a current strength of several milliamperes in a hollow-cathode lamp filled with molecular nitrogen at a pressure of less than 2 millibar to generate the radiation for the absorption measurement, that the absorption measurement be performed on at least two different characteristic absorption bands of the formaldehyde with absorption coefficients at a previously known ratio to one another which lie in the range of emissions of the gas discharge in the hollow-cathode lamp, that the ratio of the actual absorptions measured on the characteristic absorption bands be formed and compared with the previously known ratio, that in the event of non-coincidence with the previously known ratio, the interference absorption be determined and subtracted from the measured absorptions, and that in the event of coincidence with the previously known ratio, the concentration of the formaldehyde be determined from the measured absorption values or, if interference absorptions are to be subtracted, from the absorption values which have been reduced by the interference absorption.

12 Claims, 2 Drawing Sheets

METHOD AND APPARATUS FOR DETERMINING CONCENTRATION

This is a continuation of application PCT/DE86/00173, filed Apr. 23, 1986, published as WO87/02772.

The present invention relates to a method for determining the concentration of formaldehyde in a medium by an absorption measurement in the range of at least one characteristic absorption band of the formaldehyde and, in the appropriate instance, subtraction of an interference absorption which is determined by at least one absorption measurement in a wavelength range outside of the characteristic absorption band of the formaldehyde.

The invention further relates to an apparatus for performing the method with a light source for generating electromagnetic radiation, with a wavelength-selective element arranged in the path of the electromagnetic radiation, with an absorption cell containing the formaldehyde likewise arranged in this path, and with a device for measuring an intensity of the electromagnetic radiation passage through the absorption cell.

In determining the concentration of a known substance in a medium by absorption spectroscopy, the problem arises, above all, if the determination is to be very accurate, that the medium contains further substances which absorb in the range of the characteristic absorption bands of the substance to be examined, with the result that the determining of a concentration on the basis of a single absorption measurement in the spectral range of a characteristic absorption band of the substance does not produce usable results. In one case, for example, only the substance may be present, which enables clear determination of the concentration on the basis of the absorption measurement, but in another case, the substance to be determined may equally well be absent altogether, and only interference components absorb within the spectral range characteristic of the substance. This shows that an accurate and reliable determining of the concentration is not possible by means of a single absorption measurement in the presence of interference absorptions.

In the measurement of methane concentrations in a gas mixture, it is known to determine an absorption value at the maximum of a methane absorption band and to compare this value with at least two absorption values lying outside. Once this ratio deviates from a predetermined ratio for methane, the presence of an interference absorption is ascertained in this known process, and, consequently, no measurement is made (German Offenlegungsschrift (unexamined patent application) 3,334,264). In this case, certain laser diodes which emit in that absorption range which is of interest are used as light source.

It is also known in the measurement of water content in paper to measure absorptions at various points and to form ratios from these, for example, the absorption bands of free water, of cellulose and the valence vibrations of the water and the CH valence vibration of the cellulose (German Offenlegungsschrift (unexamined patent application) 2,910,673).

Finally, in the photometric determination of concentration ratios in two-component-systems, it is known to determine absorptions at various wavelengths which then provide information on the concentration ratios of the substances of interest in a highly complicated mathematical manner (German Offenlegungsschrift (unexamined patent application) 2,343,097).

To date, there are, however, no known processes for determining the concentration of formaldehyde by absorption spectroscopy which enable determination of this noxious substance occurring in the exhaust gases of motor vehicles run on liquid gas, alcohol or oil, in wood-fired furnaces and in particle board manufacture with concentrations in the ppm range, in a simple and reliable manner. Where formaldehyde occurs, acetone, higher aldehydes, benzene, olefins and similar polyatomic molecules with atomic numbers larger than those of the formaldehyde are always present as interference components. The absorption structure of these molecules has a substantially larger band width than that of formaldehyde so that, in general, its absorption spectrum is always superimposed by further interference absorptions of these molecules, which, consequently, prevents a sufficiently accurate concentration measurement in the ppm range.

The method described in German Pat. No. 2,246,365 for the elimination of additional absorptions by oil mist and soot in the absorption spectrometric determination of the concentration of nitric oxides in a gas mixture also fails to produce satisfactory results in the above-described field of application since compensation of the interference absorption by absorption measurement beside the characteristic absorption band of the nitric oxide is not reliable enough, and, above all, gives no indication as to whether on the characteristic absorption band of the nitric oxide only the absorption of this molecule is actually measured, and not also other interference absorptions.

Further known prior art methods such as mass spectroscopy and high-resolution optical spectroscopy are either not accurate enough or involve costs which do not permit commercial use of these methods, for example, as a continuous method of measurement in constant industrial operation.

The object underlying the invention is, therefore, to so improve a method of the generic kind that the concentration of formaldehyde in a medium can be determined by absorption spectroscopy using simple means and reliable measured values are produced with the necessary accuracy.

This object is attained in accordance with the invention in a method of the kind described at the outset by the features indicated in the characterizing clause of claim 1.

Use of a hollow-cathode lamp filled with molecular nitrogen at a pressure of less than approximately 2 millibar as radiation source to produce the radiation absorbed by the formaldehyde has proven particularly advantageous for determining the absorption of the formaldehyde. A gas discharge with a current strength of several milliamperes is maintained in this hollow-cathode lamp. The emitted radiation also contains radiation from the electron vibration transitions of the nitrogen molecule $C^3\pi_u \rightarrow B^3\pi_g$, the so-called second positive system. Levels C and B are excited states of the nitrogen. Atmospheric nitrogen in the ground state cannot absorb at these wavelengths.

Particularly advantageous nitrogen bands are the nitrogen bands of the 0.0 transition (3371 Ångström units), the 3.3 transition (3285 Ångström units), the 4.4 transition (3268 Ångström units), the 1.0 transition (3159 Ångström units), the 2.1 transition (3136 Ångström units), the 3.2 transition (3116 Ångström units) and the 4.3 transition (3106 Angström units). These coincide surprisingly well with absorption bands of the formaldehyde at 3387 Angström units, 3288 Angström units and 3125 Angström units, respectively.

The quasi-resonance absorption produced with formaldehyde using such a molecular nitrogn emission has the great advantage of a high sensitivity with simultaneous use of several wavelengths. These wavelengths are automatically available, i.e., in special cases, a monochromator can be dispensed with, and, for example, the measuring range of from 2950 Angström units to 3380 Angström units can be selected with an interference filter. If foreign gas absorptions with known and constant transverse sensitivity lie there, these can then be taken into account by calculation by subsequent comparison measurements.

A further great advantage of this method is that it is possible to determine by the measurement on several characteristic absorption bands of the formaldehyde whether its absorption spectrum is superimposed by further interference absorptions. This can be done either before or after determination of the interference absorptions by absorption measurement in a wavelength range outside of a characteristic absorption band. In addition to the higher accuracy of the absorption measurement due to measurements being made on various characteristic absorption bands, it is thereby simultaneously ensured that the concentration of the formaldehyde is only calculated and indicated in the case where solely the absorption of the formaldehyde is measured, whereas in all other cases where superimpositions by other interference components cannot be excluded, the concentration is not determined. Therefore, independently of whether measurement and subtraction of the interference absorption proved necessary and were carried out or did not prove necessary, the measured concentration can always be relied upon as corresponding to the actual concentration of the formaldehyde.

In contrast to known methods of absorption measurement, it is not absolutely necessary to hit the formaldehyde absorption maximum, in each case, in the absorption measurement made by this method, what is essential is simply measurement at fixed wavelengths whose absorption values are compared. These wavelengths may also lie on the edge of an absorption line.

Determination of the interference absorption in a single minimum of the absorption spectrum of the formaldehyde usually furnishes very unreliable results so that in order to eliminate the interference absorptions at least two absorption measurements are made in the range of various absorption minima of the formaldehyde to enable a more precise quantitative determination of the interference absorptions.

In the embodiments of the method described hereinabove, no indication was given as to the spectral position in which the interference absorption measurements should be made relative to the absorption measurements on the characteristic absorption bands of the substance. To determine the interference absorptions present in the range of the characteristic absorption bands as accurately as possible, it is advantageous for the measurements for determining the interference absorptions to be performed in the absorption minima neighboring on the absorption bands.

The accuracy of the determination of the concentration is further increased in the inventive method by selecting the position of the absorption minima so that the characteristic absorption bands lie between these.

In all methods wherein the interference absorption is determined by at least two interference absorption measurements, subtraction of the interference absorption is advantageously effected by a linear interference absorption spectrum being calculated on the basis of the interference absorption measurements and subtracted from the measured absorptions. In the event that more than two interference absorption measurements are made, a polynomial of a higher order can be calculated and subtracted as interference absorption spectrum.

The embodiments of the method described hereinabove all required the interference absorption spectrum either to be considered constant in the range of the characteristic absorption bands of the formaldehyde or to be linearized throughout this range or to be replaced by a polynomial of a higher order. With all other kinds of interference absorption spectra, i.e., for example, those which likewise exhibit a maximum in the range of the characteristic absorption bands, the inventive method did not indicate an incorrect value of the concentration, but, in accordance with the inventive method, it did also not determine a value of the concentration of the known substance, since the interference absorption could not be fully subtracted, and, consequently, the previously known ratio of the absorptions on the characteristic absorption bands was also not attained after subtraction of the interference absorption. This is, however, also possible in such a case provided that the interference absorption spectrum is previously known and absolute values of this absorption spectrum are determined by measurement of the interference absorption. In such a case, interference absorption spectra of very complex configuration can, therefore, also be subtracted and an accurate value of the concentration of the formaldehyde calculated by the inventive method.

If, as explained hereinabove, the previously known ratios of the absorption coefficients do not coincide approximately with the measured ratios of the absorption coefficients, the inventive method does not furnish a value of the concentration of the formaldehyde, in other words, indication of an erroneous value is avoided, but the method fails to detect the concentration of the formaldehyde. This disadvantage is eliminated in an improved embodiment of the inventive method wherein in the event that the previously known ratio is not attained after subtraction of the interference absorptions, at least two further characteristic absorption bands lying in another area of the absorption spectrum of the formaldehyde overlapping the emission spectrum of the gas discharge are selected, the ratio of the absorptions is determined and compared with the previously known value, and, in the appropriate instance, the interference absorption is ascertained and subtracted. In this case, the interference absorption can be ascertained and subtracted by any of the previously explained methods. Even if this should not permit determination of the concentration on account of the previously known ratios of the absorption coefficients still not being attained, it is always possible to select at least two further characteristic absorption bands and, in accordance with the inventive method, to ascertain or not ascertain the concentration of the known substance.

In all hitherto explained embodiments of the inventive method it is advantageous for the characteristic absorption bands to lie in a narrow spectral range so that the interference absorptions can be subtracted in as simple a way as possible since with characteristic absorption bands located as closely as possible to one another, the interference spectrum does not generally change to a very large degree within this spectral range and, consequently, the interference spectrum determined in accordance with the previously explained method steps contains less errors.

The lifetime of the apparatus used can be extended by the absorption measurements being performed in a pulsed manner. A further advantage of this method is that the pulsed absorption measurements result in an increase in the sensitivity since a commonly known lock-in method for improving the signal-to-noise ratio can also be employed in pulsed measurements.

A further object of the invention, in addition to the method described hereinabove, is to provide an apparatus for performing the method.

This object is attained, in accordance with the invention, with an apparatus of the kind described at the outset by the light source being constituted by a hollow-cathode lamp filled with molecular nitrogen at a pressure of less than 2 millibar, with a gas discharge maintained therein at a current strength of several milliamperes to furnish a line spectrum with spectral lines in the wavelength range of characteristic absorption bands and being provided for comparing them with previously known ratios of the absorption coefficients and for ascertaining and subtracting interference absorptions.

The advantage of this apparatus according to the invention is that the line spectrum of the special hollow-cathode lamp offers the possibility of carrying out the characteristic absorption bands as well as ascertaining the interference absorptions simultaneously or almost simultaneously.

To this end, the wavelength-selective element may, for example, be in the form of a dispersing element and the device for measuring the intensity of the electromagnetic radiation may comprise several channels, with each channel determining the absorption pertaining to one of the spectral lines used for the inventive method, so that the intensities for determining the absorption in the range of the characteristic absorption bands and the intensities in one or several of the absorption minima for determining the interference absorption can be measured simultaneously and made available to the computer system. Continuous measurement without time delay is, therefore, always possible. It is, however, also conceivable for the wavelength-selective element to switch very rapidly from a first to further spectral lines used in the inventive method, which renders only one detector necessary, which then measures the intensity values pertaining to the respective spectral line. This kind of light source is operated with low currents or also in a pulsed manner. It, therefore, has a very long lifetime and, in addition, furnishes very sharply defined spectral lines, which, in turn, permit a very inexpensive and simple wavelength-selective element design.

Further features and advantages of the invention are apparent from the following description and the appended drawing of an embodiment of the invention.

Figure 1:
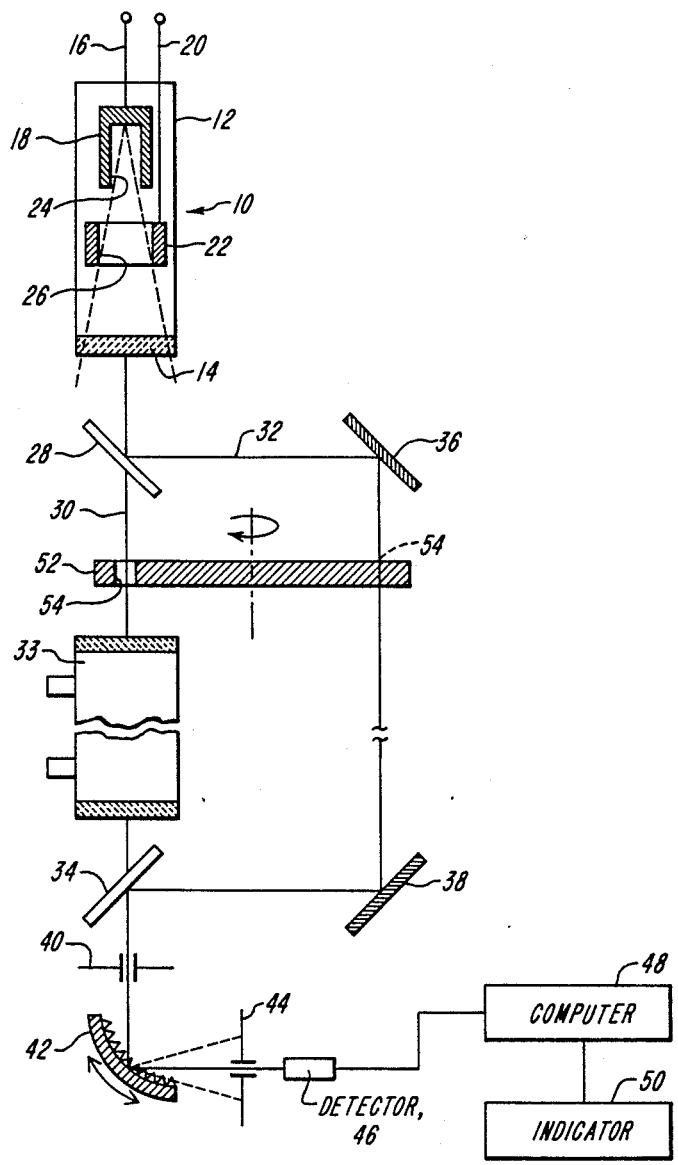
FIG. 1 shows an embodiment of the apparatus according to the invention.

FIG. 1 shows in detail a hollow-cathode lamp 10 serving as light source and comprising a casing 12 with a quartz window 14. An electric line 16 extends through the casing 12 to a hollow cathode 18, and an electric line 20 to an anode 22. The hollow cathode 18 comprises, in the usual manner, a bore 24 with an opening oriented in the direction of the quartz window 14, and the anode 22 is in the form of a ring having an inner opening 26 coaxially aligned with the bore 24 of the cathode 18.

Molecular nitrogen at a pressure of less than two millibar is used to fill the casing 12 of this special hollow-cathode lamp.

The hollow-cathode lamp 10 is normally operated by a power pack with a stabilized current, not illustrated in the drawing, so that a gas discharge with a current strength of several milliamperes takes place between cathode and anode. A hollow cathode 18 consisting of iron, chromium, nickel, cobalt is used.

This electromagnetic radiation emitted from the hollow-cathode lamp 10 exits from the hollow-cathode lamp 10 through the quartz window 14 and strikes a beam splitter 28 which divides the radiation up into a measuring beam 30 which spreads out further in the straight direction and a reference beam 32 which branches off perpendicularly thereto. The measuring beam 30 strikes an absorption cell 33 containing a substance whose concentration is to be determined by the apparatus according to the invention. Having gone through the absorption cell 33, the measuring beam 30 arrives at a beam splitter 34 and passes through it in the straight direction. The reference beam 32 which branched off at the beam splitter 28 strikes a mirror 36 where it is deflected through 90 degrees and extends parallel to the measuring beam 30 until it strikes a mirror 38 again and is reflected from it onto the beam splitter 34. The latter directs the reference beam 32 in the same direction as the measuring beam 30 so that after the beam splitter 34, both pass through an entrance gap 40 and strike a wavelength-selective element, in this case, a concave grating 42 which, as dispersing element, disperses both the measuring beam 30 and the reference beam 32 into a spectrum and deflects their individual components in a different manner.

The respectively selected components of both the measuring beam 30 and the reference beam 32 pass through an exit gap 44 and strike a detector 46. The detector 46 may be chosen from any commercially available radiation detectors such as photomultipliers, photodiodes and the like. The intensity value of the respectively selected spectral component determined in the detector 46 is recorded by a computer system 48 which, as will be described hereinafter, calculates the respective concentration of the substance in the absorption cell 33 and makes the value available to an indicator 50.

To enable switching back and forth between an intensity measurement of the measuring beam 30 and the reference beam 32, both pass through a sector shutter 52, also referred to as chopper, arranged in front of the absorption cell 33 and comprising, in the usual manner, a circular disk with openings 54 so arranged on the disk that they allow either the measuring beam 30 or the reference beam 32 to pass. By turning this sector shutter, either the measuring beam 30 or the reference beam 32 can be released alternately.

To measure the intensity of the various spectral lines used in the inventive method, the grating 42 is rotatably mounted so that it can be turned into the respective positions in which the desired spectral line passes through the exit gap 44.

The absorption measurement is performed with the apparatus illustrated in FIG. 1 as follows:

The line spectrum emitted from the hollow-cathode lamp 10 passes as measuring beam 30 through the absorption cell 33 and strikes the grating 42 which disperses the measuring beam 30 into rays corresponding to the individual spectral lines. The grating 42 is set so that the first spectral line to be examined passes through the exit gap 44 and strikes the detector 46. The detector 46 then measures the intensity of this spectral line. Rotation of the sector shutter 52 to prevent passage of the measuring beam 30 through one of the openings 54 releases, on the other hand, the reference beam 32 which strikes the grating 42 instead of the measuring beam 30 and is dispersed there into the same spectral components. Since the grating 42 is turned so that the first spectral line to be examined passes through the exit gap 44, it strikes the detector 46 and its intensity is measured there. Constant rotation of the sector shutter 52, therefore, enables the intensity of a certain spectral line emitted from the hollow-cathode lamp 10 to be measured alternately, with an intensity value of the measuring beam 30 corresponding to this spectral line being divided by the value of the reference beam 32. The apparatus for measuring the intensity must, of course, be synchronized with the rotation of the sector shutter 52 to enable recognition of whether the intensity of the measuring beam 30 or that of the reference beam 32 is being measured.

When the absorption pertaining to the first spectral line has been ascertained, the grating 42 is rotated so that the second spectral line passes through the exit gap 44 and strikes the detector 46. The absorption pertaining to the second spectral line is determined analogically. Since the absorption measurements can be performed very quickly, it is not necessary for the grating 42 to be turned through discrete angles, in each case, but instead an oscillating grating can be used so that the spectral lines pass continuously one after the other through the exit gap 44. Such an oscillating grating must, of course, also be synchronized with the apparatus for measuring the intensities to enable correlation of the individual intensity values with the individual spectral lines.

In a further preferred embodiment of the inventive apparatus, the exit gap 44 and the detector 46 are replaced by a row of detectors arranged alongside one another. These are arranged so as to each measure the intensity of one of the spectral lines into which the grating 42 disperses the electromagnetic radiation of the hollow-cathode lamp 10, and which are relevant to the inventive method, as will be described hereinafter. This eliminates the necessity of constantly turning the grating 42 back and forth, and the intensities of all relevant spectral lines can be measured simultaneously.

A further modification consists in replacing the exit gap 44 illustrated in FIG. 1 by a plurality of gaps which each allow one of the spectral lines required in the inventive method to pass through it, and to provide the exit gaps with one light guide each to guide the light to a detector, with constant switching back and forth between the various light guides being enabled by, for example, an oscillating mirror so that the detector successively measures the intensities of the light from the individual light guides.

The embodiment of the inventive apparatus illustrated in FIG. 1 may, furthermore, be simplified by elimination of the reference beam 32, which also renders the sector shutter 52, the beam splitters 28 and 34 and the mirrors 36 and 38 unnecessary. This simplified embodiment is sufficient, above all, for apparatus which do not require a very high measurement accuracy or with which very high concentrations of the substance are to be measured. In this case, the intensity of the individual spectral lines emitted from the hollow-cathode lamp 10 is measured and stored in the computer system 48 prior to introduction of the substance into the absorption cell 33.

If very low concentrations of the substance are to be determined it is imperative that the measuring beam 30 extend over as large a distance as possible within the absorption cell 33 so as to provide as long a path as possible for the absorption of the spectral lines. In such a case, a simple absorption cell 33 may be replaced by one where the measuring beam 30 is reflected back and forth several times within the absorption cell 33 and, consequently, covers a distance within the absorption cell 33 which is a multiple of one length of this absorption cell 33. Also, any of the methods for improvement of the signal-to-noise ratio such as averaging over a longer time, lock-in technique, etc. may be employed in this case.

Figure 2:
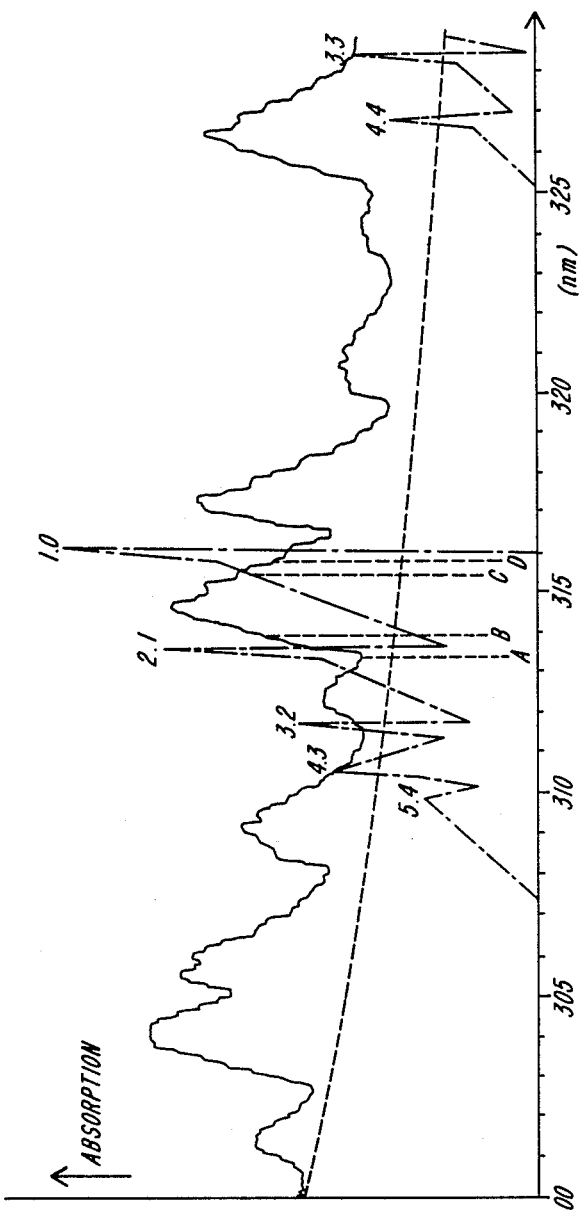
FIG. 2 shows an absorption spectrum of formaldehyde with a superimposed emission spectrum of a hollow-cathode lamp filled with molecular nitrogen.

In FIG. 2, reference is made to an absorption spectrum of formaldehyde (continuous curve) which illustrates superimposition of the actual absorption spectrum of formaldehyde by a background or an interference absorption (dashed curve). An emission spectrum of the special hollow-cathode lamp 10 is illustrated, in addition, in dot-and-dash lines. FIG. 2 shows only part of the spectral range usable for the measurment.

Since the configuration of the absorption spectrum of formaldehyde is known for the performance of the inventive method, four spectral lines designated by A, B, C and D whose spectral position is indicated in FIG. 2 are selected prior to the measurement. Lines A and D lie in the range of absorption minima of the formaldehyde and serve to determine the interference absorption, while lines B and C lie in the range of absorption bands of the formaldehyde.

The absorption at B and C is first measured, the ratio of B to C is formed and compared with the known value which was ascertained with a calibration spectrum free from interference absorption. As is apparent from FIG. 2, the ratio of B to C will definitely not coincide with the value of the calibration spectrum since there is a very strong background due to an interference absorption in this spectral range. This is detected by the method and, therefore, the interference absorption in the range of the spectral line A is first determined. This can be subtracted, for example, as constant background from the measured absorption values at B and C so that the ratio of B to C is formed with the corrected absorption values at B and C and compared with that of the calibration spectrum. If they are found to coincide, the concentration of the substance is determined on the basis of the absolute values of the absorption, i.e., the absolute values of the optical density at B and C in accordance with the Lambert-Beer law.

Subtraction of a constant interference absorption measured at A from the absorptions measured at B and C in the absorption spectrum illustrated in FIG. 2, is, however, not accurate enough and the interference absorption at D is, therefore, measured, in addition, and this value is used to calculate an interference absorption linearized between A and B. If, to some extent, there should also be an absorption of the formaldehyde at D, this is of no significance since it is known from the calibration spectrum and can, therefore, be taken into account in the calculation of the interference absorption.

The interference absorption at B and C determined by linearization of the values of the interference absorption at points A and B is then subtracted from the absorption values measured at B and C. The absorptions at B and C thus correspond with those of the actual absorption spectrum of formaldehyde so that the ratio of B to C also coincides with the ratio known from the calibration spectrum, and the concentration of the formaldehyde can be indicated with sufficient accuracy.

If in spite of subtraction of the interference absorption spectrum, the ratio of B to C should not coincide, then either a value of the concentration is not calculated, in accordance with the inventive method, which excludes indication of erroneous concentration values, or the same method is performed in the range of a further absorption band and its neighboring minima, in which case, a concentration value is likewise only calculated and indicated if the measured ratio coincides with that of the known calibration spectrum.

An assessment of the concentrations of formaldehyde which are measurable with the inventive method indicates that with an absorption coefficient of 8/cm in the range of B and a path length of the measuring beam 30 in the absorption cell 33 of approximately 60 cm, the measuring beam 30 is attenuated in accordance with the Table given hereinbelow.

| Concentration $H_2CO$ in the absorption cell 33 | Light attenuation $\Delta I/I$ of the measuring beam 30 |
|---|---|
| $c = 10^{-3}$ (1000 ppm) | 38% |
| $c = 10^{-4}$ (100 ppm) | 4.7% |
| $c = 10^{-6}$ (1 ppm) | 0.5% |

Since even light attenuations in the range of 0.5% are readily measurable by common present-day techniques, the inventive method enables measurements of formaldehyde in the ppm range and, consequently, provides the accuracy required for the fields of application mentioned at the outset.

What is claimed is:

1. Method for determining the concentration of formaldehyde in a medium by an absorption measurement in the range of at least one charactersitic absorption band of the formaldehyde and, in the appropriate instance, subtraction of an interference absorption which is determined by at least one absorption measurement in a wavelength range outside of the characteristic absorption band of the formaldehyde, characterized in that a discharge is maintained at a current strength of sufficient milliamperes in a hollow-cathode lamp filled with molecular nitrogen at a pressure of less than 2 millibar to generate the radiation for the absorption measurement, in that the absorption measurement is performed on at least two different characteristic absorption bands of the formaldehyde with absorption coefficients at a previously known ratio to one another which lie in the range of emissions of the gas discharge in the hollow-cathode lamp, in that the ratio of the actual absorptions measured on the characteristic absorption bands is formed and compared with the previously known ratio, in that in the event that the previously known ratio and the measured ration do not coincide, the interference absorptions are determined and subtracted from the measured absorptions, and in that in the event of coincidence of the previously known ratio and the measured ratio, the concentration of the formaldehyde is determined from the measured absorption values or, if interference absorptions are to be subtracted, from the absorption values which have been reduced by the interference absorption.

2. Method as defined in claim 1, characterized in that the measurement absorption lines of the formaldehyde lie in the areas overlapping the electron vibration transitions of the nitrogen molecule $C^3\pi_u \rightarrow B^3\pi_g$ (second positive system), in particular, in the range of the 0.0 transition (3371 Angström units), the 3.3 transition (3285 Angström units), the 4.4 transition (3268 Angström units), the 1.0 transition (3159 Angström units), the 2.1 transition (3136 Angström units), the 3.2 transition (3116 Angström units) and the 4.3 transition (3106 Angström units).

3. Method as defined in claim 1, characterized in that at least two absorption measurements are performed in the range of various absorption minima of the formaldehyde to eliminate the interference absorptions.

4. Method as defined in claim 3, characterized in that the measurements for determining the interference absorptions are performed in the absorption minima neighboring on the characteristic absorption bands.

5. Method as defined in claim 4, characterized in that the position of the absorption minima is so selected that the characteristic absorption bands lie between these.

6. Method as defined in claim 3, characterized in that further interference absorption measurements are performed.

7. Method as defined in claim 3, characterized in that subtraction of the interference absorption is effected by a linear interference absorption spectrum being calculated on the basis of the interference absorption measurements and subtracted from the measured absorptions.

8. Method as defined in claim 3, characterized in that a polynomial of a higher order is calculated and subtracted as interference absorption spectrum.

9. Method as defined in claim 1, characterized in that the interference absorption spectrum is previously known and its absolute values are determined by measurement of the interference absorption.

10. Method as defined in claim 1, characterized in that if the previously known ratio is not attained after subtraction of the interference absorptions, at least two further characteristic absorption bands lying in another area of the absorption spectrum of the formaldehyde overlapping the emission spectrum of the gas discharge are selected, the ratio of their absorptions is determined and compared with the previously known value and, in the appropriate instance, the interference absorption is determined and subtracted.

11. Method as defined in claim 1, characterized in that the absorption measurements are performed in a pulsed manner.

12. Device for determining the concentration of formaldehyde in a medium by an absorption measurement in the range of at least one characteristic absorption band of formaldehyde and, in the appropriate instance, subtraction of an interference absorption which is determined by at least one absorption measurement in a wavelength range outside of the characteristic absorption band of the formaldehyde with a light source for generating electromagnetic radiation, with a wavelength-selective element arranged in the path of the electromagnetic radiation, with an absorption cell containing the formaldehyde likewise arranged in this path, and with a device for measuring an intensity of the electromagnetic radiation after passage through the absorption cell, comprising said light source being a hollow-cathode lamp filled with molecular nitrogen at a pressure of less than 2 millibar, with a gas discharge maintained therein at a current strength of sufficient milliamperes to generate a line spectrum including spectral lines in the wavelength range of characteristic absorption bands (B and C) and absorption minima (A, D) of the substance, and a computer system to determine ratios between absorptions of characteristic absorption bands (B, C) and to compare them with previously known ratios of the absorption coefficients and to determine and subtract interference absorptions.

* * * * *